United States Patent [19]

Kelly

[11] Patent Number: 5,208,031

[45] Date of Patent: May 4, 1993

[54] SEXUAL LUBRICANTS CONTAINING ZINC AS AN ANTI-VIRAL AGENT

[76] Inventor: Patrick D. Kelly, 33 Berry Oaks, Glendale, Mo. 63122

[21] Appl. No.: 737,169

[22] Filed: Jul. 29, 1991

Related U.S. Application Data

[63] Continuation-in-part of Ser. No. 528,495, May 25, 1990, abandoned, which is a continuation-in-part of Ser. No. 362,058, Jun. 6, 1989, abandoned.

[30] Foreign Application Priority Data

Jun. 4, 1990 [EP] European Pat. Off. ........... 90306054

[51] Int. Cl.$^5$ ..................... A61K 7/40; A61K 31/315; A61K 33/30; A01N 55/02
[52] U.S. Cl. .................................. 424/412; 424/401; 424/405; 424/614; 514/774; 514/777; 514/781; 514/784; 514/785; 514/786; 514/886; 514/931; 514/934; 514/944; 514/966; 514/967; 514/968; 514/969
[58] Field of Search ............... 514/494, 774, 777, 781, 514/784, 785, 786, 886, 931, 934, 944, 966, 967, 968, 969; 424/401, 614, 405, 412

[56] References Cited

U.S. PATENT DOCUMENTS

| | | | |
|---|---|---|---|
| 4,407,818 | 10/1983 | Lionelle et al. | 424/289 |
| 4,465,666 | 8/1984 | Lukas et al. | 424/145 |
| 4,548,950 | 10/1985 | Baxendale et al. | 514/510 |
| 4,604,404 | 8/1986 | Munson et al. | 514/494 |

FOREIGN PATENT DOCUMENTS

87/02246 10/1987 World Int. Prop. O. .

OTHER PUBLICATIONS

Brawner, T. A., et al., "A Combined Chemical-Physical Treatment for Herpes Simplex Lesions in Guinea Pigs," *Arch. Dermatol. Res.* 265:71–77 (1979).

Brody, I., "Topical Treatment of Recurrent Herpes Simplex ... Zinc Sulphate Solution," *Brit. J. Dermatol.* 104:191–194 (1981).

Eby, G. A., and W. W. Halcomb, "Use of Topical Zinc to Prevent Recurrent Herpes Simplex Infection: Review of Literature and Suggested Protocols," *Medical Hypotheses* 17:157–165 (1985).

Fahim, M., et al., "New Treatment for Herpes Simplex Virus Type 2 [Ultrasound and Zinc, Urea, and Tannic Acid Ointment] Part 1—Male Patients," *J. Medicine* 9(3): 245–264 (1978).

Fahim, M., et al., "New Treatment for Herpes Simplex Virus Type 2. Part 2—Female Patients," *J. Medicine* 11 (2&3): 143–167 (1980).

Fahim, M. S. and Brawner, T. A., "Treatment of Genital Herpes Simplex Virus in Male Patients," *Arch. Andrology* 4: 79–85 (1980).

Tennican, P. O., et al., "The Diverse Effects of Topical and Systemic Administration of Zinc on the Virulence of Herpes Simplex Genitalis," *Life Sciences* 24: 1877–1884 (1979).

(List continued on next page.)

Primary Examiner—Thurman K. Page
Assistant Examiner—Carlos Azpuru
Attorney, Agent, or Firm—Patrick D. Kelly

[57] ABSTRACT

This invention relates to the use of zinc salts as anti-viral agents in sexual lubricants. A zinc salt which releases divalent zinc ions in an aqueous carrier fluid is provided in a sexual lubricant formulation which is spread on the genitals before sexual intercourse. The mixture is non-irritating, and the zinc ions serve as an anti-viral agent to reduce the risk of contracting genital herpes if a sexual partner is infected. These lubricants may also reduce the risk of infection by other sexually transmitted viral diseases, such as hepatitis, papilloma viruses, and AIDS. A preferred lubricant formulation comprises water, a thickening or suspending agent, a lubricating agent, and a suitable zinc salt. Salts which have been tested and shown to be non-irritating during sexual intercourse include zinc acetate, zinc propionate, and zinc gluconate. Other zinc salts have also been identified which are soluble in water and have low pK values, which indicates a high rate of zinc ion release.

8 Claims, No Drawings

OTHER PUBLICATIONS

Tennican, P., et al., "Topical Zinc in the Treatment of Mice Infected Intravaginally with Herpes Genitalis Virus," *Proc. Soc. Exp. Biol. Med.* 164: 593–597 (1980).

Wahba, A., "Topical Application of Zinc Solutions: A New Treatment for Herpes Simplex Infections of the Skin?" *Acta Derm. Venerol. (Stockholm)* 60: 175–177.

Fitzherbert, J. C., "Genital Herpes and Zinc," *Med. J. Australia*, May 5, 1979, p. 399.

Fridlender, B., et al., "Selective Inhibition of Herpes Simplex Virus Type 1 DNA Polymerase by Zinc Ions," *Virology* 84: 551–554 (1978).

Gordon, Y. J., et al., "Irreversible Inhibition of Herpes Simplex Virus Replication in BSC-1 Cells by Zinc Ions," *Antimicrob. Agents Chemother.* 8: 377–380 (1975).

Gupta, P., and Rapp, F., "Effect of Zinc Ions on Synthesis of Herpes Simplex Virus Type 2-Induced Polypeptides," *Proc. Soc. Exp. Biol. Med.* 152: 455–458 (1979).

Jones, R., "Genital Herpes and Zinc," *Med. J. Australia*, Apr. 7, 1979, p. 286.

Shlomai, J., et al., "Effect of Zinc Ions on the Synthesis of Herpes Simplex Virus DNA in infected BSC-1 Cells," *Virology* 66: 330–335 (1975).

Sergio, W., "Zinc Salts that may be Effective Against the AIDS Virus HIV," *Medical Hypotheses* 26 (4): 251–253 (1988).

Cannan, R. K., and Kibrick, A., "Complex Formation between Carboxylic Acids and Divalent Metal Cations," *J. Amer. Chem. Soc.* 60: 2314–2320 (1938).

W. L. Williams, "New Antifertility Agents . . ." *Contraception* 6(22): 659–672 (1980).

SEXUAL LUBRICANTS CONTAINING ZINC AS AN ANTI-VIRAL AGENT

This is a continuation-in-part of U.S. application Ser. No. 528,495, filed on May 25, 1990, now abandoned, which was a continuation-in-part of U.S. application Ser. No. 362,058, filed on Jun. 6, 1989, also abandoned.

BACKGROUND OF THE INVENTION

This invention is in the fields of biochemistry, pharmacology, and anti-viral agents.

There is a major need for methods to prevent the spread of viral diseases that are transmitted through sexual contact, including genital herpes, which is caused by a virus called herpes simplex virus type 2 (HSV-2). A second herpes virus called herpes simplex virus type 1 (HSV-1) is occasionally detected in genital lesions, but it is usually associated with cold sores around the mouth.

Herpes simplex viruses are complex by viral standards. They carry roughly 70,000 base pairs of double-stranded DNA, and more than 50 open reading frame sequences that can encode polypeptides have been identified in their genomes. The DNA is enclosed within a capsid made of protein molecules, and the capsid is enclosed within an envelope made of a lipid bilayer. Protein molecules that help the virus bind to and infect certain types of cells project outwardly from the outer surface of the envelope. Those protein molecules are glycosylated, i.e., sugar molecules are attached to them, which makes it more difficult for an infected animal to generate an effective immune response to the virus. For more information on herpes viruses, see, e.g., Mindel 1989, Rapp 1984, Mertz 1990, and Kono and Nakajima 1985 (complete citations to books and articles are contained below, before the claims). Mindel 1989 offers a good introduction and overview.

Once contracted, genital herpes is incurable, and in addition to causing recurrent painful lesions, it poses a serious health threat. It can cause malignant transformation in animal and human cells, and has been linked to increased risks of cervical and vulvar cancer in women. The virus can also infect babies during birth, causing neonatal herpes, which is often fatal and can cause blindness, retardation, and other severe and permanent health problems if the baby survives.

Genital herpes is also believed to play an important role in the transmission of other sexually transmitted viruses, including acquired immunodeficiency syndrome (AIDS, which is caused by the human immunodeficiency virus, HIV). In effect, herpes lesions act as wounds or breaches in the protective layers of the skin and mucosal membranes. As an epidermal cell approaches the surface, it becomes squamous (flattened) and loses its chromosomes; its amino acids and nucleotides (the building blocks of proteins, DNA, and RNA) are depleted, and it becomes relatively inert metabolically. Within a few days after an epidermal cell reaches the surface, it is sloughed off, in a process of continuous replacement as other cells from the lower layers of the epidermis approach the surface. If a virus injects DNA or RNA into an epidermal cell in the outer layer of an intact and healthy region of the epidermis, the virus is not likely to be able to replicate inside the cell, since the cell will normally be depleted of the nucleotides and amino acids the virus needs. Therefore, a healthy and intact epidermal layer provides a major barrier against viral infection, but that barrier is breached by herpes lesions, which provide vulnerable entry sites for invading viruses. If someone with genital herpes has intercourse with someone else who has HIV or some other sexually transmitted virus, the person with herpes is more likely than a non-herpetic would be to contract AIDS or another disease as a result. In addition, in people infected with both herpes and the HIV virus (as is the case with many prostitutes), herpes lesions presumably can increase the number of infectious HIV viral particles emitted by the infected person, since white blood cells infected by the HIV virus are likely to be present in the fluid in the herpes lesions, trying to fight the herpes virus. Therefore, any method for preventing the spread of genital herpes can help slow down the spread of AIDS and other sexually transmitted viruses.

The need for ways to reduce the spread of herpes and AIDS are especially acute in view of the severe difficulties that have been encountered in trying to develop vaccines that can prevent infection by either virus. Despite intensive effort, there has been little progress in developing successful and effective vaccines against either virus.

The most widely recommended protective measure to prevent the spread of herpes, AIDS, and other sexually transmitted viruses (including papilloma, hepatitis, and Epstein-Barr viruses) requires the use of a condom during intercourse. However, even though numerous health care professionals, government officials, and the scientific, medical, and mass media have repeatedly urged all sexually active non-monogamous people to use condoms, many people at risk either fail or refuse to follow that advice.

Therefore, there is an urgent need for additional ways to reduce the spread of sexually transmitted viral diseases. As used herein, the term "anti-viral" is used broadly, to refer to an agent or method which can inhibit the replication or emission of viruses, or which can reduce the likelihood that a person or animal exposed to potentially infective viral particles will contract the viral disease, regardless of which stage or step of the viral cycle or transmission process is inhibited.

Anti-Viral Zinc in the Prior Art

Zinc is a mineral that is present in all forms of life, including human life. Among the transition metals, it is second in abundance in mammals only to iron, and if hemoglobin is discounted, zinc is even more abundant than iron. Zinc is necesssary for a wide variety of metabolic processes, including the synthesis as well as the degradation of nucleic acids, proteins, carbohydrates, and lipids. It also stabilizes the three-dimensional conformation of a number of enzymes known as "zinc finger proteins." For a review of the roles of zinc in metabolism, see Vallee 1988; for a review of the roles zinc plays in the immune system, see Bach 1981.

Several studies have reported that various salts which release divalent zinc ions ($Zn^{++}$) can inhibit the replication of some types of viruses. Those studies include Gordon et al 1975 (herpes virus), Bracha et al 1976 (sindbis virus), Firpo et al 1979 (foot and mouth disease virus), Zaslavsky et al 1979 (vaccinia viruses), and Sharma et al 1985 (aphthovirus).

The effects of zinc on rhinoviruses (a class of viruses which cause common colds) have also been studied, but the results have been inconsistent. Korant et al 1976A and 1976B reported that zinc ions can inhibit the replication of some but not all rhinoviruses in cell culture. Eby et al 1984 reported that in a double-blind test, tablets made of zinc gluconate (a common salt sold over-the-counter as a vitamin supplement), when chewed up and allowed to remain in the mouth, reduce cold symptoms. Eby obtained U.S. Pat. No. 4,503,070 (1985) on the use of zinc gluconate lozenges to treat cold symptoms. That patent was followed by U.S. Pat. No. 4,684,528 (Godfrey 1987) on flavor-masked zinc lozenges.

Eby's positive reports provoked a series of rhinovirus studies which led to negative results, including Douglas et al 1987, Farr et al 1987, and Geist et al 1987. Some of the factors that apparently contributed to the confusing and inconsistent results include concentration and chelation, which are discussed with a severe lack of clarity and consensus in the letters gathered at Godfrey et al 1988. That exchange of letters shows that the people studying the effects of zinc on rhinoviruses are divided on the question of whether it works; in addition, those who claim that it works cannot explain why. The most extensive study done to date, Al-Nakib et al 1987, stated, "We conclude that zinc gluconate lozenges . . . have a significant effect on the signs and symptoms of colds caused by rhinoviruses, although the mechanism of action remains obscure."

One of the factors that may be contributing to the confusion and disagreements over rhinoviruses is that some strains of rhinovirus may be resistant to inhibition by zinc, in a manner analogous to the way some bacteria are resistant to antibiotics. For example, the Inventor has chewed zinc gluconate tablets a number of times to fight colds since learning about Eby's U.S. Pat. No. 4,503,070. In most cases, the zinc was highly effective and either stopped the cold entirely or greatly reduced its severity. However, in two or three specific instances, it seemed to have little effect.

Another factor that may have contributed to the confusion over zinc and rhinoviruses involves the apparent need for direct contact between the zinc ions and the virus. On several occasions when the Inventor chewed zinc gluconate tablets to fight colds, he ended up with a severe runny nose as well as soreness in the lower throat, but with no adverse symptoms in the mouth. Those results strongly indicate that the antiviral action of zinc depends upon direct contact of the zinc ions with the viral particles. However, several of the rhinovirus studies tried to evaluate zinc by applying it in the mouth and then determining whether it could prevent a cold that was induced by injecting viral particles into the nose via nasal sprays. Similarly, some of the assays for effectiveness involved nasal washings, to determine how many viable virus particles remained in the nasal sinuses; however, the zinc had been applied to the mouth rather than the nasal sinuses. Since zinc apparently requires direct contact with viruses to be effective, those approaches were inadequate to provide a fair test; they are analogous to testing an antibiotic ointment against bacteria by applying the ointment several inches away from a skin cut.

At least five different research teams have reported that certain salts of zinc, used by most researchers in combination with other active agents such as tannic acid or heparin, are effective as topical agents in treating genital herpes lesions. A team in Missouri led by Dr. Mostafa Fahim reported that guinea pigs and humans (both male and female) suffering from genital herpes improved substantially when treated by a combination of ultrasound and an ointment containing 30% urea, 3% zinc sulfate, 2% tannic acid, and 65% HEB cream; see Fahim et al 1978, Brawner et al 1979, Fahim et al 1980a, and Fahim et al 1980b.

In Arizona, a team led by Dr. Patrick Tennican reported that female mice which had been inoculated with herpes virus, and female humans seeking treatment for genital herpes, improved when a collagen sponge containing zinc sulfate was placed inside the vagina; see Tennican et al 1979 and Tennican et al 1980.

In Israel, Dr. Asher Wahba reported that 4 patients with genital herpes showed improvement after being treated with zinc sulfate in water; see Wahba et al 1980.

In Texas, George Eby and Dr. William Halcomb reported that solutions of zinc gluconate in water accelerated recovery in four human females suffering from herpes; see Eby and Halcomb 1985.

And in Switzerland, Bohumir Lukas et al disclosed that a mixture of zinc sulfate and a solfated polysaccharide such as heparin inhibited herpes in tissue culture tests and in guinea pigs; see U.S. Pat. Nos. 4,465,666 and 4,762,715 and Canadian Pat. No. 1,146,859, assigned to Ciba-Geigy.

There have also been reports that zinc solutions help people suffering from non-genital herpes, including cold sore lesions in the mouth (see Wahba et al 1980 and Brody et al 1981) and keratitis lesions in the eyes (see DeRoeth et al 1963).

The work by Lukas et al is a good example of the apparent attitude of most medical researchers toward the use of zinc to combat herpes infections. In column 3 of U.S. Pat. No. 4,465,666, Lukas et al reported that zinc sulfate, when mixed with a gel carrier and applied to guinea pigs three days after the guinea pigs were infected with herpes viruses, reduced the number of guinea pigs suffering from observable symptoms. As described by Lukas, about 50% of the animals treated with the gel base alone were free of herpes symptoms, but if zinc was added to the gel, about 70% of the animals were free of symptoms. However, Lukas et al criticized that result and pointed out that an additional improvement could be obtained by adding both zinc and heparin to the gel. When both zinc sulfate and heparin were used, about 95% of the animals were free of symptoms.

The Lukas et al experiments indicate that heparin mixed with zinc provides a more effective treatment than zinc alone, in animals that had been previously infected with herpes. However, heparin is a powerful anti-coagulant; it prevents blood from clotting normally. Therefore, even though a compound containing heparin might be used safely under the supervision of a physician for several days, the typical duration of a herpes outbreak that is properly treated, it would be highly inadvisable to administer heparin to anyone on a frequent basis, such as every night for weeks or months. It would also be inadvisable to sell heparin for use as an over-the-counter drug without a prescription. It is clear that Lukas et al did not recognize or anticipate the potential of zinc, without heparin, in a form that can be used frequently as a sexual lubricant to provide an antiviral protective agent for people who are not yet infected by herpes. In addition, as indicated by the experiment described below in Example 5, although zinc sulfate does not irritate the male genitals, it irritates the mucosal membranes of the vagina and is likely to cause irritation if used during male-female intercourse.

U.S. Pat. No. 4,407,818 (Lionelle and Staffa, 1983) discloses the use of a molecular complex which is not a salt, zinc hexakis(acetato)oxotetra, for treating viral, bacterial, and fungal infections. The compound, which has a formula of $C_{12}H_{18}O_{13}Zn_4$, is shown in a three-dimensional representation in Koyama and Saito 1954 with a single oxygen surrounded by four zinc atoms in a tetrahedral configuration, with six organic residues coupled to the four zinc atoms. Lionelle and Staffa reported that in in vitro tests, this molecular complex inhibited herpes simplex virus.

All of the reports cited above which involve zinc salts involved the use of the zinc salts to treat herpes lesions or to prevent the recurrence of outbreaks in animals or people who are already infected with herpes. To the best of the inventor's knowledge, no one has previously suggested the use of zinc as a preventive agent in a lubricant formulation to be used during actual intercourse, to inhibit the transmission of herpes to someone who is not previously infected.

In a patent application filed under the Patent Cooperation Treaty, number WO 8702246, William Sergio suggested that the risk of infection with AIDS might be reduced by topical administration of compounds that generate anions having charges greater than one. Sergio's reference to anions appears to be mistaken, since an anion is a negatively charged ion, while zinc ions are cations (positively charged). Sergio also states that his preferred salts are zinc phosphonoformate and/or zinc tungstate; however, it is likely that the use of either of those compounds in a sexual lubricant would cause irritation to the mucous membranes and perhaps to the epidermis as well, and might cause various other adverse effects. His suggestion concerning zinc tungstate appears to be based on the tungsten compound HPA-23, which, as Sergio conceded elsewhere, has "serious side effects" (Sergio 1988).

There remains, therefore, a need for a sexual lubricant which is effective as an anti-viral agent, which is non-toxic, and which is non-irritating to the genitals and urethral and vaginal membranes even when rubbed in vigorously, as occurs during sexual intercourse.

One object of this invention is to provide a non-irritating anti-viral sexual lubricant that can be used during intercourse by people who do not suffer from herpes infections, who wish to minimize their risk of contracting herpes or other sexually transmitted viruses.

Another object of this invention is to provide a non-irritating anti-viral sexual lubricant that can be used by people who have herpes but who insist on having unprotected sex and exposing unwitting partners to the disease. Although such conduct is unethical and immoral, it cannot be stopped by either law or societal pressure, as evidenced by the presence of prostitution in every large city anywhere in the world. It would help slow the spread of herpes and protect the public if a non-irritating anti-viral sexual lubricant were available for use by prostitutes and other promiscuous people who have genital herpes.

SUMMARY OF THE INVENTION

This invention relates to the use of soluble zinc salts as anti-viral agents in sexual lubricants. A zinc salt which releases zinc ions in an aqueous carrier fluid is provided in a sexual lubricant formulation which is spread on the shaft of the penis or inside the vagina before sexual intercourse. The lubricant does not irritate the genital skin or mucous membranes of a person who is uninfected by genital herpes, and the zinc ions serve as an anti-viral agent to reduce the risk of contracting genital herpes if a sexual partner is infected. These lubricants may also reduce the risk of infection by other sexually transmitted viral diseases, such as hepatitis, papilloma viruses, and AIDS. A preferred lubricant formulation comprises water, a thickening or suspending agent such as hydroxyethylcellulose, a lubricating agent such as glycerin or polyethylene glycol, and a suitable zinc salt. Salts which have been tested and shown to be non-irritating during intercourse include zinc acetate, zinc propionate, and zinc gluconate.

DETAILED DESCRIPTION OF THE INVENTION

This invention involves a sexual lubricant containing a zinc salt which inhibits the replication of herpes virus. As used herein, "sexual lubricant" refers to a fluidized substance which is spread on the shaft of the penis or inside the vagina shortly before or during sexual intercourse, and which remains in contact with the shaft of the penis or the vaginal canal during intercourse. It does not include ointments or other fluidized substances that are spread on the genitals for purposes other than to provide a lubricant coating during sexual intercourse; for example, it does not include ointments intended to promote the healing of herpes lesions during an active outbreak.

When the lubricants of this invention are used during sexual intercourse, the zinc ions released by the zinc salt dissolved in the lubricant reduce the risk that an uninfected person will become infected by genital herpes if the sexual partner emits herpes simplex virus. This invention relates to the discovery that some zinc salts that are soluble in aqueous solutions do not irritate the skin or mucosal membranes of the penis or vagina, even when a lubricant mixture containing such a salt is rubbed in over a sustained period of time, as occurs during intercourse.

The lubricants of this invention preferably should be used in addition to a condom for maximal protection, but they can also be used without a condom for a lesser but still significant level of increased protection compared to unprotected intercourse.

Since most people who use sexual lubricants prefer to use water-soluble lubricants that can be washed off easily after intercourse without leaving a residue, most of the discussion below focuses on water-soluble gels. "Gel" is used herein to refer to an aqueous mixture which contains a thickening agent (as discussed below) and which has a viscous or semi-solid form at room temperature. Preferably, a sexual lubricant gel should become less viscous as it warms up from room temperature to physiological temperature (37° C. or 98.6° F.). The high viscosity at room temperature allows the gel to be applied conveniently before intercourse, without dripping off the fingers or genitals onto bedsheets or other surfaces. After intercourse begins and the gel warms up, it becomes less viscous and more slippery, providing comfortable lubrication during intercourse.

Gels can be mixtures of molecular components that are completely dissolved and non-particulate, such as an aqueous fluid containing a soluble polymer as the thickening agent. Alternately, gels can be suspensions or colloidal solutions, which contain insoluble particles suspended in a liquid carrier medium. The suspended particles are usually microscopic in size, with average diameters measured in microns (for suspensions) or angstroms (for colloids). There is no clear-cut boundary between colloidal and soluble gels. For example, when powdered cellulose is mixed with water, the cellulose particles (which are hydrophilic) swell up and soften, so that they are no longer hard "particles" as that term is normally used, and some cellulose derivatives become transparent in water. These effects blur the distinctions between gel suspensions and soluble gels.

One water-soluble gel which has a variety of desired characteristics and which is widely used as a sexual lubricant is sold under the name "K-Y Lubricating Jelly" (Johnson and Johnson, New Brunswick, N.J.). It contains purified water, hydroxyethylcellulose as the suspending or thickening agent, glycerin as a lubricant, glucono-delta-lactate to prevent crystallization, chlorhexidine gluconate as a preservative, and sodium hydroxide to reduce the acidity. Those ingredients will be discussed in more detail below. A modified form of KY Lubricating Jelly sold by Johnson and Johnson contains propylene glycol residuals, which are a by-product of propylene oxide, a sterilizing agent.

Some types of emulsions and hydrophobic compounds also act in a manner comparable to gels, and they can be used as sexual lubricants if desired. Emulsions are two-phase liquid systems containing tiny immiscible droplets or globules of one fluid suspended in a carrier liquid (see, e.g., Becher 1965). Many emulsions are more expensive than typical gels; they usually require a time-consuming emulsification step during manufacturing to ensure that the inhomogenous fluids are finely and evenly dispersed throughout the mixture, and they usually require the use of a chemical surfactant (usually a molecule similar to a detergent, with a hydrophobic portion at one end and a hydrophilic portion at the other end) to keep the suspended droplets from coalescing and separating. In addition, emulsions and hydrophobic compounds (such as petroleum jelly) tend to leave residues that can be difficult to wash off, and some can weaken condoms, causing them to break. For these reasons, emulsions and hydrophobic compounds are not preferred by most people as lubricants during intercourse. However, it was stated in Shilts 1987 that vegetable shortening is used as a sexual lubricant by some male homosexuals who engage in frequent anal intercourse; in addition, some people like to use petroleum jelly. Presumably, since such compounds do not rub off or rinse away easily, they offer prolonged lubrication compared to water-soluble lubricants. Accordingly, an emulsion or hydrophobic carrier substance can be used as a vehicle for an anti-viral zinc salt if desired. Any such formulation should be tested in vivo as described below to determine whether it is anti-virally effective. As used herein, terms such as "aqueous carrier fluid" and "aqueous substance" are broad enough to include an emulsion having an aqueous component.

Suspending or Thickening Agents

In suspensions and emulsions, agents that increase the viscosity of the carrier liquid are often used to prevent the insoluble particles or immiscible droplets from coalescing, settling to the bottom, or floating to the surface. In soluble gels, such agents are used to thicken the mixture and help ensure that all of the molecular components remain in a stable suspended condition and do not separate into layers based on density differences. Such agents are called suspending agents or thickening agents; as used herein, the terms "suspending agent" and "thickening agent" are used interchangeably.

Numerous types of physiologically-acceptable thickening agents are used in pharmaceutical and cosmetic preparations; see, e.g., pages 1304-1308 in *Remington's Pharmaceutical Sciences* (Gennaro 1990). These include compounds derived from plants, seaweed, or bacteria, such as powdered cellulose, chemically-treated cellulose derivatives such as hydroxyethylcellulose, acacia (also called gum arabic), agar, alginic acid and its salts (such as sodium alginate), carrageenan, gum tragacanth, and xanthan gum. Other substances derived from animals, such as lanolin (an exudate secreted by sheep into wool fibers) and gelatin (a mixture containing collagen, a protein) are also used as thickening agents in cosmetics and other skin care products. Various synthetic chemicals are also used, including carbomer (a common name for carboxypolymethylene), glyceryl monostearate, and povidone (polyvinylpyrrolidone). A mixture containing polyacrylamide in water, which functioned as both a thickening agent and a lubricating agent in a "physiological mucus" which assertedly was a suitable sexual lubricant, is described in U.S. Pat. No. 3,965,908 (Posthuma and Woodhouse 1976). Minerals such as colloidal silicon dioxide or clay are also used in some formulations.

Most sexual lubricant gels that are commercially available contain cellulose derivatives as suspending or thickening agents. Certain derivatives such as hydroxyethylcellulose, which generate a clear and relatively transparent gel rather than a milky-white or opaque gel, are preferred since they minimize staining of bedsheets, pajamas, and clothing.

Any physiologically acceptable thickening agent can be used as described herein, provided that: (1) it must provide suitable levels of viscosity; (2) preferably, the viscosity should decrease somewhat as the gel warms up from room temperature to physiological temperature; (3) it must be non-irritating to the genitals and mucous membranes when used as a sexual lubricant; and (4) it must not severely reduce the anti-viral activity of the zinc ions, as can be determined by in vivo testing using herpes virus as described below.

Lubricating Agents

As used herein, "lubricating agent" refers to a chemical substance, other than water, which is incorporated into a sexual lubricant mixture for the purpose of reducing friction during intercourse. Although any liquid (including water) can sometimes function as a "lubricant" in the broadest sense of the word, four characteristics distinguish a "lubricating agent," as that term is used herein, from water and other liquids which do not have the characteristics necessary for effective lubrication in the context of sexual intercourse.

First, lubricating agents useful for sexual intercourse feel slippery and substantially more viscous than water when rubbed between the fingers. Second, lubricating agents should have an affinity for human skin; when applied to skin, they should spread smoothly and evenly across the contacted area. Third, a lubricating agent should remain in contact with the skin, clinging to it in a more substantial manner than water, which is easily wiped away. And fourth, a lubricating agent should have a low level of volatility; it should not evaporate quickly. The foregoing characteristics can easily be recognized and understood on a practical level by rubbing a lubricating agent such as glycerin or mineral oil between the fingers. The nature and the durability of the lubrication provided by such a compound, and the differences between such agents and other liquids such as water, are readily apparent.

A lubricating agent which is "physiologically acceptable for use during sexual intercourse" should not cause significant adverse effects (such as irritation, tenderness, swelling, redness, or skin discoloration) when used as a sexual lubricant, and does not pose a significant risk as a carcinogen or teratogen. In addition, in contrast to non-physiological lubricants such as motor oil, physiologically acceptable lubricating agents should be either gradually broken down into innocuous substances in the body, if they are absorbed through the skin or mucous membranes, or they should be of a nature that allows them to be secreted by the vagina and washed cleanly from the skin, so that they will not foul and clog the pores in epidermal layers. Several lubricating agents which are used in commercially available sexual lubricants satisfy these criteria, including glycerin (also called glycerine, glycerol, 1,2,3-propanetriol, and trihydroxypropane) and certain types of polyethylene glycol (PEG), such as PEG 200 or PEG 400 (the numbers indicate different molecular weight averages). Various other polymers (such as polypropylene glycol, polyisobutene, and polyoxyethylene) and behenic acid and behenyl alcohol are also used as lubricants in cosmetics and other formulations that contact the skin. In addition, some sugar-alcohols such as sorbitol and some silicon compounds such as polydimethylsiloxane are also used as skin-contacting lubricating agents.

Because glycerin, propylene glycol, polyethylene glycol, and polypropylene glycol have long been used in sexual lubricants and other skin-contacting formulations with no adverse effects, they are preferred for use as lubricating agents in the anti-viral sexual lubricants of this invention. The suitability of any other candidate lubricating agent in a sexual lubricant as described herein can be determined through routine experimentation in humans to ensure that it will not cause irritation or other adverse effects, and in in vivo tests as described below to ensure that a formulation containing the candidate lubricating agent is anti-virally effective.

Additional Agents

Various other components, including preservatives (such as chlorhexidine gluconate), anti-crystallization agents (such as glucono-delta-lactate), fragrances, coloring agents, alkaline or acidic agents to maintain the proper pH, and soothing or anti-swelling agents such as lanolin, aloe vera extract, or hydrocortisone can be added to the sexual lubricants described herein, provided that (1) any such additive should not seriously impede the anti-viral activity of the selected zinc salt due to reactions such as chelation or the formation of covalently-bonded zinc-containing molecular complexes, and (2) the additive should not irritate or have other adverse effects on the genitals.

Many cosmetics, shampoos, and other topically applied mixtures contain alcohols, detergents, or other chemicals that would irritate the skin if applied in concentrated form, but which are acceptable in low concentration, especially if any irritating effects are suppressed or masked by soothing or anti-swelling agents. Accordingly, a lubricant gel can contain a small quantity of a compound that might be an irritant if present in concentrated form, provided that the formulation as a whole does not cause irritation.

Ointments and Lotions

Various ointment, lotion, and cream formulations are known to those skilled in the art; many of those can function as carriers for active ingredients. Several are described in detail in the *U.S. Pharmacopeia* and in various standard texts on cosmetics. In general, ointments, lotions, and creams are not as widely suitable as aqueous gels for use as sexual lubricants, for several reasons, including: (1) they often contain undesired ingredients which can be irritating and/or unnecessarily expensive, such as alcohols or emulsifiers; (2) they usually do not have the type of desirable temperature-dependent viscosity that sexual lubricant gels have; and, (3) most ointments and many lotions and creams are hydrophobic and cannot be washed off easily.

Despite those drawbacks, various ointment, lotion, or cream formulations can be used as vehicles to carry the zinc salts of this invention if desired, provided that they do not render the zinc salt ineffective as an anti-viral agent, and provided that no components are present in concentrations that irritate the genitals or mucous membranes.

Skin and Vaginal Irritation Tests

To be suitable for use as described herein, a specific zinc salt must not irritate the genitals when present in a formulation that has anti-viral activity (as used herein, the term "genitals" includes the mucosal membranes inside the vagina and urethra). The level of genital irritation caused by any candidate formulation can be determined by using tests involving human volunteers, who should be fully informed of the entire procedure. It should be made clear to the volunteers that irritation tests do not involve viruses and do not pose any risk of infection; their sole purpose is to determine whether a certain zinc salt or carrier formulation irritates the genitals, and if so, what percentage of the population is affected by such irritation (as discussed below). Whenever such tests are done, the subject population should not include women who might become pregnant during the course of the test.

A preferred sequence of tests is as follows. In the first test, a selected zinc salt is first tested on the relatively hairless portion of the forearm. If a zinc salt is used which is not highly soluble in water, a mortar and pestle can be used to grind the particles into a fine powder; alternately, if a salt is used which is highly soluble, stirring will be adequate. Distilled water should be used to dissolve or suspend the salt and spread it across a relatively small area of skin.

If the zinc salt does not cause irritation after being left in place for an hour or more, the next test in the series of escalating tests involves spreading it upon the male genitals, which can be washed off more quickly and easily than female genitals if irritation occurs. The first test on the male genitals should involve a passive test; the zinc salt is suspended or dissolved in water, applied gently, and allowed to remain without rubbing it in, for a period such as an hour.

If the zinc salt causes no irritation in the passive test (or if it causes only mild irritation when mixed with water, as discussed below), the next test involves mixing the zinc salt with a gel lubricant such as K-Y Lubricating Jelly, applying it to the male genitals, and rubbing it in for several minutes in a manner that simulates the effects of intercourse.

If it causes no irritation in the active rubbing test on male volunteers, the zinc salt can be dissolved in a suitable gel carrier and applied gently to a female volunteer, to the interior region near the opening of the vaginal canal which can be reached with shallow penetration. The woman should have tissues and a douche available before the test begins, to wipe and rinse out the substance if it begins to cause irritation.

During a passive test, zinc acetate caused a brief, relatively mild level of irritation in the vaginal tract of a female volunteer when dissolved in distilled water, but it caused no irritation when mixed with K-Y Lubricating Jelly. Similarly, zinc propionate caused substantial irritation to the male urethra when mixed with water alone, but it caused no irritation when mixed with K-Y Lubricating Jelly. Accordingly, part of this invention rests on the discovery that some zinc salts, although irritating to the genitals when mixed with water only, are non-irritating when mixed with a complete lubricant formulation such as K-Y Lubricating Jelly. Accordingly, it is recommended that any test of irritation using female volunteers should use a complete lubricating gel formulation (such as K-Y Lubricating Jelly) as the carrier agent during the tests.

If the zinc compound causes no irritation in the shallow passive test on female volunteers, it can be applied to the deeper areas inside the vagina, using a finger to apply it and rub it in gently.

If no irritation occurs in those tests, the mixture can be tested during actual intercourse, using a gel such as K-Y Lubricating Jelly as a carrier. During the first test involving intercourse, the gel mixture containing the zinc salt preferably should be applied and tested only after a first act of coitus has been completed during which both partners climax, so that if irritation does occur, neither person will be left in a state of sexual frustration, which aggravates any feelings or irritation.

It must be kept in mind that people vary in their skin sensitivity. By way of illustration, some people sunburn quickly, while others can withstand prolonged direct sunlight. In addition, some people are highly susceptible to any mental suggestion of possible irritation, especially when such a suggestion involves sexual matters. Some people complain about (and occasionally even display measurable symptoms) even when nothing more than an inert placebo is administered to the genitals. Reichman 1985 provides a good example; during tests of acyclovir cream applied topically to herpes lesions, identical fractions (29.6%) of the men in both the treated (acyclovir) and the untreated (placebo) groups complained of a burning sensation, regardless of whether they were treated with acyclovir or with the innocuous placebo. Among women, the level of complaints of a burning sensation were nearly identical (53.3% for the acyclovir group, and 52.6% for the placebo group). The placebo consisted of polyethylene glycol, which is completely non-irritating in most situations, even when applied directly to active herpes lesions, as evidenced by the fact that over 70% of the men and nearly 50% of the women tested made no complaints of any burning sensation.

Accordingly, anyone studying the irritation level of any zinc-containing sexual lubricant should anticipate some complaints about irritation. The important criterion for evaluation of irritation is whether such complaints rise to a statistically significant level above the number of complaints provoked by placebo treatments.

In view of the widely varying skin sensitivity of different people, and in view of the high susceptibility of some people to any suggestion of potential irritation, references herein to "non-irritating" zinc salts or formulations refer to salts or formulations that do not cause irritation in a substantial number of the people tested. Such formulations can be used by a substantial fracton of the population, even though they may cause irritation in other people who have higher levels of sensitivity or who are more susceptible to psychosomatic suggestions of irritation.

Anti-viral Zinc Salts

Zinc salts which are suitable for use as described herein must have a substantial degree of anti-viral activity, as discussed below. Such activity is presumed to arise from the presence of dissociated divalent zinc ions ($Zn^{++}$). Three factors are important in determining the concentration of zinc ions that will be present in an aqueous carrier substance if a certain zinc salt is dissolved in the carrier substance. Those factors are:

(1) The solubility of the zinc salt in water. This value is usually expressed in terms of grams of salt per 100 cubic centimeters (0.1 liter) of saturated solution. That figure can be converted into a grams/liter basis by multiplying it by 10.

(2) The molecular weight of the salt, which allows a weight concentration to be converted into a molar concentration. For example, the molecular weight of zinc acetate is 183.4, so 183.4 grams of zinc acetate is equal to one mole ($=6.02 \times 10^{23}$ molecules). Molar concentrations are usually expressed in molar (M) units, which refer to moles of a compound per liter of solution, or in millimolar (mM) concentrations, which refer to thousandths of a mole per liter.

(3) The rate at which the salt dissociates into cations and anions. This is usually expressed on a base 10 logarithmic scale using pK values, which are often called equilibrium constants, stability constants, or dissociation constants. If a pK is low, the rate of ionic dissociation for that particular salt is high.

Published solubility and pK values for several zinc salts are provided in Table 1. From a review of several articles cited by Sillen and Martell 1964 and 1971, it appears that for the salts listed in Table 1, reported pK values of less than 2 refer to the release of a single carboxy anion from a zinc salt, which occurs twice in the following two-step reaction:

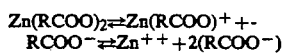

By contrast, reported pK values of more than 2 (e.g., Griesser et al 1968) apparently relate to both steps of the two-step dissociation reaction. There are several different methods for measuring ion concentration, and variations in measured values between different published papers reflect differences in the method of measurement.

TABLE 1
PROPERTIES OF VARIOUS ORGANIC SALTS OF ZINC

| Salt | Solubility (grams/liter) | Molecular weight | Molar solubility (moles/liter) | Reported pK values |
|---|---|---|---|---|
| Zinc acetate | 300 (25° C.) | 183.4 | 1.64 | 1.03 |
| Zinc propionate | 320 (15° C.) | 211.5 | 1.51 | 1.01 |
| Zinc butyrate | 107 | 275.6 | 0.4 | 1.00 |
| Zinc formate | 52 (20° C.) | 155.4 | 0.33 | $pK_1 = 0.6$, $pK_2 = 0.95$ |
| Zinc gluconate | 127 (25° C.) | 455.7 | 0.28 | 1.70 |
| Zinc glycerate (dihydroxypropionate) | NA | 275.6 | NA | 1.80 |
| Zinc glycolate (hydroxyacetate) | NA | 215.5 | NA | 1.92 |
| Zinc lactate | 57 | 279.5 | 0.20 | 1.86 |

Sources: L. G. Sillen and A. E. Martell, Stability Constants of Metal Ion Complexes, 1964 and 1971 CRC Handbook of Chemistry and Physics, 71st Edition (D. R. Lide, ed.), p. 4-116 to 118 Solubility of Inorganic and Metal Organic Compounds, 4th Edition (W. F. Linke, ed.) R. K. Cannan and A. Kibrick, J. Amer. Chem. Soc. 60: 2314 at 2317 (1938)

Since zinc gluconate has already been reported to be effective in combatting established herpes infections, it can be regarded as a benchmark of effectiveness. Other zinc salts that are comparably soluble or more soluble, and which have comparable or lower pK values compared to zinc gluconate, can be presumed to be effective in inhibiting herpes virus. The anti-viral effectiveness of any such zinc salt in aqueous solution, or in a complete lubricant formulation, can be tested using in vitro tissue culture tests or in vivo animal tests as described below.

Organic Salts

All of the organic zinc salts listed in Table 1 are good candidates for use in anti-viral lubricants as described herein. Other organic salts that appear to be less preferred, since they are less soluble in aqueous solution and/or because they have relatively high pK values, include zinc salicylate, zinc citrate, zinc oleate, zinc benzoate, zinc laurate, and zinc tartrate.

Two preferred salts that have high solubility and high ionic dissociation are zinc acetate and zinc propionate. As described in Examples 1 and 2, both have been tested for irritation; although both caused vaginal irritation when dissolved in water alone, they were found to be non-irritating when mixed with K-Y Lubricating Jelly and used as a lubricant during intercourse. Zinc butyrate also has a high rate of ionic dissociation; however, since it is less soluble than zinc acetate or propionate, it was not tested for irritation.

Several other organic salts of zinc were obtained and evaluated, including zinc stearate, zinc salicylate, and zinc valerate. None of those salts caused any irritation during forearm or male genital tests; however, each had other drawbacks. Zinc valerate, although soluble in water, has an unappealing dirty-looking color and an unpleasant odor. Zinc stearate and zinc salicylate have very low solubility in water, and also have unpleasant odors. Accordingly, even though they caused no irritation in forearm or male genital tests, they were not tested vaginally or during intercourse.

Zinc gluconate was tested as described in Example 3 and did not cause any irritation during intercourse. Zinc gluconate is formed when a single atom of zinc reacts with two atoms of gluconic acid, a carboxylic acid derivative of glucose, a sugar molecule that contains six carbon atoms. Although published data on the solubility or pK values for zinc salts formed from other sugar-acids are not easily available, the chemical structures of the sugar-acids suggests that zinc salts formed from carboxylic acid derivatives of other sugars are likely to be comparable to zinc gluconate in solubility and pK values. For example, the only differences between glucose, galactose, and mannose involve the orientation of the hydroxyl groups on the carbon atoms. Such differences may be important in enzyme chemistry, but they are likely to have little or no effect on solubility or ionic dissociation. Accordingly, zinc salts formed from carboxylic acid derivatives of sugars other than glucose are likely to be comparable to zinc gluconate in solubility and dissociation, the major aspects that determine the release of divalent zinc ions. As used herein, "sugar" is used in the standard chemical sense, to refer to polyhydroxylated aldehydes and ketones. Lists of the most common sugars are contained in organic chemistry or biochemistry texts, such as Loudon 1984 at pages 1384 and 1424-1428, and Lehninger 1975 at pages 250-251 and 261-262. A number of sugar-acids (including gluconic acid, glucaric acid, glucuronic acid, galacturonic acid, and mannuronic acid) are discussed at Lehninger 1975 pages 258-259. Any of these sugar-acids are suitable candidates for use as described herein.

The organic salts listed in Table 1 were derived from monocarboxylic acids; the organic constituents used to form these salts contain only one carboxyl (—COOH) group, and each molecule of salt is formed by coupling two organic moieties to one atom of zinc. There are a number of dicarboxylic acids which contain two carboxyl groups at different locations on a single molecule; examples include oxalic acid, malonic acid, malic acid, maleic acid, fumaric acid, succinic acid, tartaric acid, and glutaric acid. One molecule of such an acid can form a salt with one molecule of zinc. Several zinc salts formed from dicarboxylic acids are soluble in water, and reportedly release divalent zinc ions at rates comparable to salts formed from monocarboxylic acids (Cannan and Kibrick 1938, at page 2319). Accordingly, any zinc salt formed from a dicarboxylic acid can be tested as described herein to determine whether it is irritating to the genital skin and membranes. Non-irritating salts which are adequately soluble can be used as described herein.

Although zinc gluconate has been tested and shown to be effective against herpes, it should be noted that zinc acetate and zinc propionate are substantially more soluble in water than zinc gluconate. In addition, in a direct comparison using consistent methodology, zinc acetate and propionate were shown to release more zinc ions than zinc gluconate (in Table IV in Cannan and Kibrick 1938, the pK values for zinc acetate and propionate were reported to be 1.03 and 1.01, while the reported value for zinc gluconate was 1.70). Accordingly, at the present time, there does not appear to be any pressing need to carefully evaluate zinc salts formed from sugar-acids. Although they are suitable candidates and can be used if desired, zinc acetate and zinc propionate appear to be preferred.

Inorganic Salts

Three inorganic zinc compounds (zinc chloride, zinc sulfate, and zinc oxide) were tested.

Zinc chloride dissolved in water caused a significant level of irritation in the forearm test, and was not tested further.

Zinc sulfate dissolved in water did not cause any irritation in the passive forearm or male genital tests. In addition, zinc sulfate mixed with K-Y Lubricating Jelly and applied to the male genitals in an active test did not cause any irritation. However, when mixed in K-Y Lubricating Jelly at a concentration of about 3% w/v, zinc sulfate caused some irritation when applied to the shallow areas of a vagina. Although the level of irritation was not severe, it was not tested during actual intercourse. Since zinc acetate and zinc propionate caused no irritation whatever, no effort was made to test zinc sulfate further, using tactics such as diluting the concentration or adding other ingredients to suppress or mask its irritating effect. However, the fact that zinc sulfate did not cause any irritation to male genitals suggests that it would be suitable for use by at least some people, such as male homosexuals.

Zinc oxide was also tested and found to be non-irritating during intercourse. It was expected to be non-irritating, since it is the main active ingredient in Desitin ointment, which is spread on baby bottoms and genitals to cure diaper rash, and in various other ointments such as opaque sunburn prevention ointments.

Zinc oxide is not a salt in the normal chemical sense; it is formed when an atom of oxygen forms a double-bond with an atom of zinc. Spontaneous dissociation of zinc oxide to release free zinc ions would be expected to be low; however, there may be enzymes or metabolic pathways that break apart zinc oxide to release zinc ions. Therefore, the potential of zinc oxide to function as an anti-viral agent should not be ignored, especially in view of its other therapeutic benefits when applied topically. Accordingly, although the Inventor is not aware of any published reports indicating that zinc oxide has anti-viral activity, its anti-herpetic activity can be determined through in vivo tests as described below. If it is shown to have anti-viral properties, it might be suitable for use according to this invention. However, it should also be noted that zinc oxide is bright white; most people prefer clear, transparent gels for use as sexual lubricants.

Packaging; Article of Manufacture Claims

The anti-viral sexual lubricants described herein preferably should be packaged in either of two types of packages, either of which can increase the convenient and consistent use and therefore the effectiveness of the anti-viral lubricants described herein.

One type of package comprises a watertight tube made of deformable metallic foil. Such tubes, which are usually crimped at one end and closed by a removable cap at the other end, are commonly used to hold toothpaste, ointments, and gels such as K-Y Lubricating Jelly and contraceptive gels. When squeezed to dispense a quantity of lubricant, a deformable metallic tube will not seek to regain its original shape after the squeezing pressure is released. By avoiding the creation of a vacuum inside the tube which would draw air into the tube, this minimizes oxidative discoloration or degradation of the lubricant in the tube. An additional advantage of a metallic container in this aprticular context is that it can be placed, preferably with the cap securely fastened and pointing down, in a cup or glass of warm or hot water, such as on a table or nightstand next to a bed. The metallic walls of the tube convey heat from the warm water into the lubricant; this warms the lubricant to a pleasant temperature before it is applied. This procedure encourages consistent rather than sporadic use, which increases the level of protection provided by the lubricant.

A second preferred type of package comprises a small, flat, watertight plastic packet which contains a sufficient quantity of lubricant for a single use during intercourse (such as about 5 to 10 milliliters, or about 1 to 2 teaspoons). This type of sealed packet allows the lubricant to be conveniently and discretely carried in a purse, pocket, or other location without the bulk or conspicuousness of a metallic tube. It also allows the lubricant to be conveniently warmed up, by immersing the packet in warm water.

This invention also teaches an article of manufacture comprising a sexual lubricant and packaging material as described above, wherein the sexual lubricant contains a zinc salt and a lubricating agent as described herein, and wherein the lubricant is contained within the packaging material, and wherein the packaging material indicates to consumers that the lubricant contained therein is to be applied to the genitals and used as a lubricant during sexual intercourse. Since about 1970, the courts have held that printed information on an article of manufacture does not remove the article from the realm of patentability, so long as the item and the invention as a whole satisfy the other requirements of the statute, such as novelty and non-obviousness. Since the zinc-containing formulations taught in the prior art by Lukas et al, Eby and Halcomb, Wahba, Fahim et al, Tennican et al, and Lionelle and Staffa (cited and summarized in the background section, above) teach zinc formulations that are intended to be applied to active herpes lesions, rather than used as a lubricant during intercourse, this article of manufacture embodies a new and non-obvious invention that is distinct and different from the prior art.

Lubricants Having A Range of Concentrations

Rather than trying to determine a single concentration of a zinc salt that would be optimal for everyone, the effectiveness of this invention can be enhanced by selling lubricants having a range of different zinc concentrations for different people. By way of analogy, since some people are easily sunburned while others are highly tolerant of direct sunlight, suntan oils and creams are sold with a range of "sun protection factors" and any purchaser is free to choose his or her preferred formulation, based not only on skin type, but also on his or her anticipated exposure. As another example, contraceptive gels sold over-the-counter contain 1% to 4% nonoxynol, and purchasers are free to choose the concentration they prefer.

In a comparable manner, sexual lubricants having a range of concentrations of anti-viral zinc salts can be made available, and people having varying sensitivities, sexual habits, and levels of concern over sexually transmitted viruses can choose the concentrations they prefer. Highly sexually active, non-monogamous people who live in cities with high rates of genital herpes might choose to use a lubricant containing 10 or 20% or more of a zinc salt, while people at lesser risk might prefer to use a formulation having a lower concentration such as 0.5 to 3%. Accordingly, this invention anticipates lubricants containing zinc salts in the range of about 0.5% to about 20%, expressed as weight per volume (w/v, calculated as grams of zinc salt per milliliter of fluid, multiplied by 100 to convert the ratio to a percentage).

As used herein, references to "low levels of irritation" refer to formulations that cause no irritation, or acceptably low levels of irritation, in at least some people. Such formulations can be used by such people regardless of whether they might cause irritation in other people who are more susceptible. In addition, the anti-viral lubricants of this invention can be used even though they may cause some irritation in the user; many people would regard a low level of mild irritation as a reasonable and necessary price for an added level of safety, comparable to the loss of sensitivity that accompanies condom use.

In Vitro Tests

Any zinc salt or other zinc compound can be tested for anti-viral activity using in vitro tests. In vitro tests involve cell cultures rather than intact animals; see, e.g., Kern 1990 and Gordon et al 1975.

Some in vitro assays involve growing anchorage-dependent cells (such as fibroblasts, which are replicating cells that generate connective tissue) on a semi-solid surface, such as on solidified agar nutrient in a petri dish. This forms a layer or "lawn" of cells evenly spread across the surface of the culture plate. A liquid solution containing infective viruses is administered to the layer of cells. In some tests, the liquid will contain the potential anti-viral agent being tested; in other tests, the anti-viral agent can be added to the cells either before or after the viruses are administered. The cells and viruses are incubated to give the viruses time to kill the cells, then the petri dishes are examined to determine how many clusters of cells were killed by the viruses, as evidenced by clear areas called "plaques" where the cells have been killed. The result of such a test is usually expressed in terms of "plaque-forming" viruses per volume of solution. If a potential anti-viral compound reduces the number of plaques, it has in vitro anti-viral activity.

Another type of in vitro assay involves stirred solutions of cells that are not anchorage-dependent, such as white blood cells, or anchorage-dependent cells that are growing on the surfaces of tiny beads. These tests often use viral "titers" (i.e., liquid solutions containing varying concentrations of viruses in a series of dilutions, wherein each dilution usually contains one tenth as many viruses as the previous dilution. Instead of measuring plaques that remain stationary on a solid surface, the number of cells that remain alive after the viral challenge can be measured. However, rather than displaying the results as the number of cells that remain alive at the end of the test, the results of viral titer assays are usually expressed in terms of the concentration of viruses in the most dilute solution which wipes out cell cultures. If a certain zinc salt allows a cell culture to withstand a concentration of viruses that would kill the cells in the absence of the zinc salt, then that salt has in vitro anti-viral activity.

Most viruses infect only certain types of cells; for example, herpes viruses infect fibroblast and epidermal cells, while the AIDS virus infects certain types of white blood cells. Therefore, cells that are susceptible to infection by a specific virus must be used in any test involving that virus.

For the purposes of this invention, a zinc salt is regarded as having in vitro anti-viral activity if it significantly inhibits one or more types of sexually transmitted virus. It is not necessary for a certain zinc salt to inhibit all types of sexually transmitted viruses in order to be useful as described herein. Even if an anti-viral sexual lubricant directly inhibits only one type of herpes virus, it is still useful in at least two respects. First, it can directly inhibit the spread of that particular herpes virus. And second, it can indirectly help reduce the spread of AIDS and other sexually transmitted viruses, by reducing the number of people who suffer from herpes lesions and by reducing the severity or duration of outbreaks of recurrent herpes lesions. As mentioned previously, herpes lesions can serve as entry and exit ports for sexually transmitted viruses other than herpes; therefore, they increase the spread of AIDS and other viral diseases.

In Vivo Tests

In vivo tests involve intact living animals or humans, as distinct from in vitro tests involving cell cultures. Although some types of in vivo tests involve inoculation of liquid solutions containing herpes through routes such as subcutaneous injection, any in vivo tests to assess the anti-viral effectiveness of an anti-viral zinc salt as described herein should involving contacting the viruses with the genitals, to simulate sexual transmission. This can be done by inserting cell-free viral solutions, or infected cells containing viruses, into the vaginas of female animals, or into the urethral mucosa of male animals.

The tests described herein can be performed on any animal species that is susceptible to herpes simplex viruses. Since rodents are much less expensive than larger animals, most tests involving herpes virus are done on mice and guinea pigs; see, e.g., Kern 1984, Kern 1988, Kern 1990, and Tennican et al 1980. In guinea pigs, in the absence of an anti-viral agent, some animals usually die, but among the animals that survive, the pattern of infection is similar to infection in humans. An initial or primary infection arises within a few days after exposure, and the initial outbreak subsides after a period of roughly a week. The initial outbreak is followed by recurrent "secondary" outbreaks, which usually occur every few weeks, and which can be induced for testing purposes by various methods such as exposing the animal to ultraviolet light. In mice, herpes infections do not follow the normal pattern seen in infected adult humans. Herpes is highly lethal in mice, due to viral encephalitis which attacks the brain and central nervous system. However, mice are sometimes used in tests requiring large numbers of animals for statistical purposes.

Tests of candidate zinc salts or lubricant formulations as described herein can follow the normal testing mode involving mechanical inoculation into the genitals, as described in the articles by Kern, cited above. Alternately or additionally, the testing of candidate formulations can involve intercourse between infected and uninfected animals.

Candidate formulations can also be tested using human volunteers who have genital herpes. Such tests preferably should be performed on people suffering from active outbreaks of lesions, preferably during the "rising red" phase of the outbreak, when a tingling or burning sensation signals the probable onset of lesions. The lubricant is applied to the genitals and massaged in for several minutes, to simulate the type of intimate skin contact and mixing that occurs during intercourse. At various times after the lubricant is administered (such as 24, 48, and 72 hours later, with appropriate follow-up monitoring), the volunteer is examined for the number and severity of lesions, and body fluids such as urine, semen, vaginal fluid, or lesion exudate can be sampled to determine the quantity of infective viral particles being shed at a given time by the volunteer. If the number of infective particles shed by treated volunteers is reduced compared to untreated control subjects, then the particular formulation being tested has in vivo anti-viral activity.

Anyone buying such a lubricant should be clearly warned that the lubricant does not offer completely reliable, 100% protection against herpes infection. Nevertheless, the anti-viral sexual lubricants of this invention can reduce the risk of becoming infected. Accordingly, in the absence of any effective vaccines or cures for herpes or AIDS, most rational people who are sexually active and non-monogamous would prefer to take the precaution of using a non-irritating lubricant which offers a significant level of added protection.

Method Claims

In addition to a composition of matter, this invention also relates to a method of reducing the risk of contracting genital herpes. The method involves spreading an aqueous mixture on the genitals before sexual intercourse, wherein the aqueous mixture comprises a physiologically acceptable carrier substance and a selected zinc salt at a concentration which inhibits herpes simplex virus, and wherein the aqueous mixture does not irritate genital surfaces or mucous membranes when used during intercourse as a sexual lubricant by an uninfected person.

Although carrier fluids that contain all the ingredients that would make a formulation a complete sexual lubricant are preferred, they are not necessary to practice the method of this invention. This invention involves two new and important discoveries: (1) various zinc salts are non-irritating, even when applied to the male genitals and the interior of a vagina and vigorously rubbed in for a sustained period during sexual intercourse; and (2) a non-irritating zinc salt can be used, not just to treat people who are already infected, but to prevent uninfected people from becoming infected. Those discoveries are different and distinct from the prior art teachings, which merely show that zinc can be used to treat herpes infections that have already become established. Accordingly, the method of using a zinc salt as an anti-viral topical agent during sexual intercourse, rather than waiting until after an infection has become established, is an invention that deserves suitable protection. From an anti-viral perspective, the carrier fluid is relatively inert biologically; its only real purpose is to deliver the anti-viral zinc salt to the intended location. Accordingly, the method claims should not be limited by the details of the carrier fluid which contains the zinc salt.

Similarly, this method is not limited to organic salts of zinc. The anion released by the salt is not critical to this invention, so long as the salt does not irritate the genitals when included at a desired concentration in a specific carrier formulation. Inorganic salts such as zinc sulfate can be used if desired, particularly in lubricant formulations that are not intended for vaginal contact, such as by male homosexuals. The prior art Lukas et al in particular) teaches compositions of matter comprising gels containing zinc sulfate; however, the prior art does not teach or suggest any method of using such salts in lubricants, during sexual intercourse. Accordingly, the method claims below are broad enough to encompass inroganic salts, provided that such salts are non-irritating and anti-virally effective when incorporated into a sexual lubricant.

EXAMPLES

EXAMPLE 1: ZINC ACETATE

In all examples, the test subjects were a monogamous married couple free of genital herpes.

Zinc acetate was purchased from Pfaltz and Bauer (Waterbury, Conn.). About 0.5 grams were mixed with several drops of distilled water at room temperature. Upon stirring, the salt dissolved completely. The aqueous mixture was rubbed into an area about 3 cm in diameter on the forearm of the male and caused no irritation. Subsequently, about 0.5 grams of the salt were dissolved in a few drops of distilled water, then 10 ml K-Y Lubricating Jelly was added to form a gel mixture containing about 5% zinc acetate (w/v). This mixture was tested on the male genitals, passively at first and then with active rubbing. It caused no irritation in either test.

When 0.5 grams of zinc acetate was dissolved in distilled water and applied to the shallow region of the vagina by the female volunteer, it caused an unpleasant tingling or mild burning sensation that subsided within about ten seconds. However, when mixed with K-Y Lubricating Jelly (5% w/v as above) and applied to the shallow region of the vagina in a gel mixture, it caused no tingling, burning, or other unpleasant sensation in a passive test. Subsequently, it was applied and used as a sexual lubricant during intercourse. Both people wiped off the excess with a tissue after intercourse, but neither person showered or washed off the lubricant until the following day. It caused no irritation to either person.

EXAMPLE 2: ZINC PROPIONATE

Zinc propionate was purchased from Pfaltz and Bauer. About 0.5 grams were dissolved in several drops of distilled water and tested on the male's forearm and genitals. Although no irritation occurred on the skin in either location, the aqueous mixture caused substantial irritation to the urethral membranes.

About 10 ml of K-Y Lubricating Jelly was added to the aqueous mixture, to create a gel mixture of about 5% w/v, which was tested, passively at first and then actively, on the male's genitals. It did not cause any irritation in either test. Another quantity of a 5% w/v gel mixture was prepared and tested passively in the shallow regions of the female's vagina. It caused no irritation, so it was used as a lubricant during intercourse. Both people wiped off the excess with a tissue after intercourse, but neither person showered or washed off the lubricant until the following day. It caused no irritation to either person.

EXAMPLE 3: ZINC GLUCONATE

Zinc gluconate was purchased from Ruger Chemical Company (Irvington, N.J.). It came in the form of a white granular powder which was gritty and interspersed with hard granules of varying sizes. About 0.5 grams were ground into a fine powder for several minutes using a mortar and pestle. The grinding was repeated after several drops of distilled water were added, and again after 10 ml of K-Y Lubricating Jelly was added. The concentration of the zinc gluconate in the gel mixture was about 5% w/v.

The mixture of zinc gluconate and K-Y Lubricating Jelly was tested on the forearm, male genitals, and female genitals. It caused no irritation, so it was applied and used as a lubricant during intercourse. Although the finely ground particles in the gel displayed a very slight roughness when rubbed hard between the forefinger and thumb, no abrasion was noticeable by either person during intercourse. Both people wiped off the excess with a tissue after intercourse, but neither person showered or washed off the lubricant until the following day. It caused no irritation to either person.

EXAMPLE 4: ZINC STEARATE, SALICYLATE, AND VALERATE

Zinc stearate, zinc salicylate, and zinc valerate were purchased from Pfaltz and Bauer. All three salts were tested for irritation on the forearm and male genitals, and none caused any irritation. However, due to other drawbacks, they were not tested during intercourse. Zinc stearate and zinc salicylate are insoluble in water, even when mixed with hot water and ground for several minutes using a mortar and pestle. In addition, both have strong unpleasant odors. Zinc valerate, although soluble in water, has an unappealing dirty-looking color and a strong unpleasant odor.

EXAMPLE 5: ZINC SULFATE

Zinc sulfate in crystalline form was purchased from Sigma Chemical Company (St. Louis, Mo.). One gram was ground into a fine powder using a mortar and pestle, then 15 ml of K-Y Jelly was added and thoroughly mixed. The mixture did not cause any irritation to the male's forearm, genital skin, or urethra, even when rubbed in actively. However, it caused a tingling or burning sensation when applied in a passive test to the female, so it was not tested during intercourse.

EXAMPLE 6: ZINC CHLORIDE

Zinc chloride in crystalline form was purchased from Sigma Chemical Company (St. Louis, Mo.). One gram was ground into a fine powder using a mortar and pestle, then dissolved in water and applied to the forearm of the male. It caused a burning sensation and was not tested further.

EXAMPLE 7: ZINC OXIDE

Zinc oxide ointment (Walgreens Pharmaceutical Laboratories, Chicago, Ill.) was tested in a genital irritation experiment. Zinc oxide, which is not a "salt" in the normal chemical sense, is known to cause little or no irritation. An ointment sold under the trade name "Desitin" (Pfizer, Inc., New York City), which contains 40% zinc oxide, is spread on baby bottoms to control diaper rash and other skin irritations. Other zinc oxide ointments are also applied to the skin for various purposes, such as on the nose to prevent sunburn. One such ointment, sold at Walgreen's (Walgreen Laboratories, Chicago, Ill.), contains 20% zinc oxide in an ointment base of white wax, petrolatum, and mineral oil. In skin irritation tests using that zinc oxide ointment, tests on the forearm or male genitals were deemed unnecessary. Approximately 5 ml of the 20% zinc oxide ointment was mixed with K-Y Lubricating Jelly to reduce the viscosity of the zinc ointment. The mixture was tested passively by the woman to ensure that it did not cause any irritation, then it was used as a lubricant during intercourse. Other than being a bit sticky and viscous, it did not cause any significant irritation to either person.

The subject invention has been described and exemplified by reference to certain preferred embodiments. However, those skilled in the art will recognize, or may ascertain using routine experimentation, various equivalents to the specific embodiments discussed herein. Such equivalents are within the scope of the invention, which is limited solely by the claims below.

REFERENCES

Al-Nakib, W., et al, "Prophylaxis and treatment of rhinovirus colds with zinc gluconate lozenges," *J. Antimicrob. Chemother.* 20: 893–901 (1987).

Asculai, S. S., et al, "Inactivation of herpes simplex viruses by nonionic surfactants," *Antimicrob. Agents Chemother.* 13: 686–690 (1978).

Bach, J.-F., "The multi-faceted zinc dependency of the immune system," *Immunology Today*, pp. 225 et seq., November 1981.

Becher, P., *Emulsions: Theory and Practice*, 2nd ed., Amer. Chem. Soc. Monograph #162 (Reinhold Publ., New York, 1965).

Bracha, M. and M. J. Schlesinger, "Inhibition of Sindbis virus replication by zinc ions," *Virology* 72: 272–277 (1976).

Brawner, T. A., et al, "A Combined Chemical-Physical Treatment for Herpes Simplex Lesions in Guinea Pigs," *Arch. Dermatol. Res.* 265: 71–77 (1979).

Brody, I., "Topical treatment of recurrent herpes simplex . . . zinc sulphate solution," *Brit. J. Dermatol.* 104: 191–194 (1981).

Cannan, R. K., and Kibrick, A., "Complex Formation between Carboxylic Acids and Divalent Metal Cations," *J. Amer. Chem. Soc.* 60: 2314 (1938).

DeClerq, E. and Walker, R. T., eds., *Antiviral Drug Development* (Plenum Publishing, N.Y., 1988).

DeRoeth, A., "Treatment of herpetic keratitis," Am. J. Ophthalmol. 56: 729–731 (1963).

Douglas, R. M., et al, "Failure of effervescent zinc acetate lozenges to alter the course of upper respiratory tract infections in Australian adults," *Antimicrob. Agents Chemother.* 31: 1263–1265 (1987).

Eby, G. A., et al, "Reduction in duration of common colds by zinc gluconate lozenges in a double-blind study," *Antimicrob. Agents Chemother.* 25: 20–24 (1984).

Eby, G. A., and W. W. Halcomb, "Use of topical zinc to prevent recurrent herpes simplex infection: review of literature and suggested protocols," *Medical Hypotheses* 17: 157–165 (1985).

Fahim, M., et al, "New Treatment for Herpes Simplex Virus Type 2: Male Patients," *J. Medicine* 9(3): 245–264 (1978).

Fahim, M., et al, "New Treatment for Herpes Simplex Virus Type 2: Female Patients," *J. Medicine* 11(2&3): 143–167 (1980).

Fahim, M. S. and Brawner, T. A., "Treatment of Genital Herpes Simplex Virus in Male Patients," *Arch. Andrology* 4: 79–85 (1980).

Farr, B. M., et al, "Two randomized controlled trials of zinc gluconate lozenge therapy of experimentally induced rhinovirus colds," Antimicrob. Agents Chemother. 31: 1183–1187 (1987).

Firpo, E. J., and E. L. Palma, "Inhibition of foot and mouth disease virus and procapsid synthesis by zinc ions," *Arch. Virol.* 61: 175–181 (1979).

Fridlender, B., et al, "Selective inhibition of herpes simplex virus type 1 DNA polymerase by zinc ions," *Virology* 84: 551–554 (1978).

Galasso, G. J., et al, eds., Antiviral Agents and *Viral Diseases of Man* (Raven Press, N.Y., 1990).

Geist F. C., et al, "In vitro activity of zinc salts against human rhinoviruses," *Antimicrob. Agents Chemother.* 31: 622–624 (1987).

Gennaro, A. R., ed., Remington's Pharmaceutical Sciences, 18th Edition (Mack Publ., Easton, Pa. 1990).

Godfrey, J. C., et al, Letters to the Editor, *Antimicrobial Agents and Chemotherapy* 32: 605–609 (1988).

Gordon, Y. J., et al, "Irreversible inhibition of herpes simplex virus replication in BSC-1 cells by zinc ions," *Antimicrob. Agents Chemother.* 8: 377–380 (1975).

Griessar, R., et al, *Inorg. Nuclear Chem. Letters* 4: 443 (1968).

Kern, E. R., "Treatment of Genital Herpes Simplex Virus Infections in Guinea Pigs," pp. 617–636 in Rapp 1984.

Kern, E. R., "Animal Models as Assay Systems for the Development of Antivirals," pp. 149–172 in De-Clerq and Walker 1988.

Kern, E. R., "Preclinical Evaluation of Antiviral Agents: In Vitro and Animal Model Testing," pp. 87–123 in Galasso et al, 1990.

Kono, R., and Nakajima, A., eds., *Herpes Viruses and Virus Chemotherapy: Pharmacological and Clinical Approaches* (Excerpta Medica, N.Y., 1985).

Korant, B. D. and B. E. Butterworth, "Inhibition by zinc of rhinovirus protein cleavage: interaction of zinc with capsid polypeptides," *J. Virol.* 18: 298–306 (1976).

Korant, B. D., et al, "Zinc ions inhibit replication of rhinoviruses," *Nature* 248: 588–590 (1976).

Koyama, H. and Saito, Y., "The crystal structure of zinc oxyacetate, $Zn_4O(CH_3COO)_6$" *Bulletin of the Chemical Society of Japan* 27(2): 112–114 (March 1954).

Lide, D. R., ed., *CRC Handbook of Chemistry and Physics*, 71st Edition (Boca Raton, Fla., 1990).

Linke, W. F., ed., *Solubility of Inorganic and Metal Organic Compounds*, 4th Edition.

Mertz, G. J., "Herpes Simplex Virus," pp. 265–300 in Galasso et al 1990.

Miller, C. J., et al, "An SIV Model for the Heterosexual Transmission of AIDS," 1989 *AAAS Annual Meeting Abstracts*, p. 47 (Amer. Assn for the Adv. of Science; 1989).

Mindel, A., *Herpes Simplex Virus* (Springer Verlager, New York, 1989).

O'Brien, J. J. and Campoli-Richards, D. M., "Acyclovir: an updated review of its antiviral activity, pharmacokinetic properties, and therapeutic efficiency," *Drugs* 37: 233–309 (1989).

Rapp, F., ed., *Herpesvirus* (Alan R. Liss, N.Y., 1984).

Reichman, R. C., "Treatment of genital herpes simplex infections with topically administered antiviral drugs," pp. 149–154 in Kono and Nakajima 1985.

Robinson, J. R. and Lee, V. H., eds., *Controlled Drug Delivery* (Marcel Dekker, New York, 1987).

Sergio, W., "Zinc Salts that may be Effective Against the AIDS Virus HIV," *Medical Hypotheses* 26(4): 251–253 (1988).

Sharma, R., et al, "Antiviral effect of zinc ions on aphthovirus in BHK-21 cell line," *Acta Virol.* 29: 517 (1985).

Shilts, R., *And The Band Played On*, St. Martin's Press, New York, 1987.

Sillen, L. G., and Martell, A. E., *Stability Constants of Metal Ion Complexes*, Special Publication No. 17 (The Chemical Society, London, 1964).

Sillen, L. G., and Martell, A. E., *Stability Constants of Metal Ion Complexes*, Special Publication No. 25 (The Chemical Society, London, 1971).

Singh, B., et al, "Virucidal effect of certain chemical contraceptives on type 2 herpesviruses," *Amer. J. Obstet. Gynecol.* 126: 422–425 (1976).

Tennican, P. O., et al, "The Diverse Effects of Topical and Systemic Administration of Zinc on the Virulence of Herpes Simplex Genitalis," *Life Sciences* 24: 1877–1884 (1979). Also see *Hospital Practice*, January 1979, pp. 44–53.

Tennican, P., et al, "Topical Zinc in the Treatment of Mice Infected Intravaginally with Herpes Genitalis Virus," *Proc. Soc. Exp. Biol. Med.* 164: 593–597 (1980).

Vallee, B. I., "Zinc: biochemistry, physiology, toxicology and clinical pathology," *Biofactors* 1(1): 31–36 (1988).

Wahba, A., "Topical Application of Zinc Solutions: A New Treatment for Herpes Simplex Infections of the Skin?" *Acta Derm. Venerol. (Stockholm)* 60: 175–177 (1980).

Weiner, R. G., "AIDS and Zinc Deficiency," *J. Amer. Med. Assn.* 252: 1409–1410 (1984).

Zaslavsky, V., "Inhibition of vaccinia virus growth by zinc ions: effects on early RNA and thymidine kinase synthesis," *J. Virology* 29: 405–408 (1979).

I claim:

1. An article of manufacture comprising a sexual lubricant mixture contained within a watertight deformable metallic container which allows the sexual lubricant mixture to be conveniently warmed before use during intercourse by immersing the metallic container in warm water, wherein the sexual lubricant mixture consists of a hydrophilic gel comprising:
   a. water;
   b. a thickening agent selected from the group consisting of cellulose and chemically treated derivative thereof, acacia, agar, alginate, carrageenan, gum tragacanth, xanthan gum, collagen, carboxypolymethylene, glyceryl monostearate, polyvinylpyrrolidone, and polyacrylamide;
   c. a lubricating agent selected from the group consisting of glycerin, propylene glycol, polyethylene glycol, polypropylene glycol, polyisobutene, polyoxyethylene, behenic acid, behnyl alcohol, sorbitol, and polydimethylsiloxane; and,
   d. a zinc salt which releases zinc ions when dissolved in the aqueous carrier substance, at an effective concentration which reduces the risk of transmission of herpes simplex virus from an infected person to an uninfected person by means of sexual intercourse, wherein the sexual lubricant is physiologically acceptable for use as a sexual lubricant during intercourse and does not irritate genital surfaces or mucous membranes of a person uninfected by genital herpes when used during intercourse as a sexual lubricant.

2. The article of manufacture of claim 1 wherein the zinc salt is selected from the group consisting of zinc acetate, zinc propionate, zinc butyrate, zinc formate, zinc gluconate, zinc glycerate, zinc glycolate, zinc lactate, and zinc sulfate.

3. The article of manufacture of claim 1, wherein the packaging material indicates that the sexual lubricant mixture contained therein is to be spread upon genital surfaces during sexual intercourse.

4. The article of manufacture of claim 1, wherein the packaging material indicates that the sexual lubricant mixture contained therein can reduce the risk of becoming infected by at least one type of sexually transmitted virus if it is spread upon genital surfaces during sexual intercourse.

5. An article of manufacture comprising a sexual lubricant mixture contained within a watertight plastic packet which contains a sufficient quantity of the sexual lubricant mixture for use as a lubricant during an act of intercourse, wherein the sexual lubricant mixture consists of a hydrophilic gel comprising:
   a. water;
   b. a thickening agent selected from the group consisting of cellulose and chemically treated derivative thereof, acacia, agar, alginate, carrageenan, gum tragacanth, xanthan gum, collagen, carboxypolymethylene, glyceryl monostearate, polyvinylpyrrolidone, and polyacrylamide;
   c. a lubricating agent selected from the group consisting of glycerin, propylene glycol, polyethylene glycol, polypropylene glycol, polyisobutene, polyoxyethylene, behenic acid, behenyl alcohol, sorbitol, and polydimethylsiloxane; and,
   d. a zinc salt which releases zinc ions when dissolved in the aqueous carrier substance, at an effective concentration which reduces the risk of transmission of herpes simplex virus from an infected person to an uninfected person by means of sexual intercourse, wherein the sexual lubricant is physiologically acceptable for use as a sexual lubricant during intercourse and does not irritate genital surfaces or mucous membranes of a person uninfected by genital herpes when used during intercourse as a sexual lubricant.

6. The article of manufacture of claim 5 wherein the zinc salt is selected from the group consisting of zinc acetate, zinc propionate, zinc butyrate, zinc formate, zinc gluconate, zinc glycerate, zinc glycolate, zinc lactate, and zinc sulfate.

7. The article of manufacture of claim 5, wherein the packaging material indicates that the sexual lubricant mixture contained therein is to be spread upon genital surfaces during sexual intercourse.

8. The article of manufacture of claim 5, wherein the packaging material indicates that the sexual lubricant mixture contained therein can reduce the risk of becoming infected by at least one type of sexually transmitted virus if it is spread upon genital surfaces during sexual intercourse.

* * * * *